US007558371B2

(12) United States Patent
Park et al.

(10) Patent No.: US 7,558,371 B2
(45) Date of Patent: Jul. 7, 2009

(54) METHOD OF GENERATING X-RAY DIFFRACTION DATA FOR INTEGRAL DETECTION OF TWIN DEFECTS IN SUPER-HETERO-EPITAXIAL MATERIALS

(75) Inventors: Yeonjoon Park, Yorktown, VA (US); Sang Hyouk Choi, Poquoson, VA (US); Glen C. King, Yorktown, VA (US); James R. Elliott, Yorktown, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 12/254,150

(22) Filed: Oct. 20, 2008

(65) Prior Publication Data

US 2009/0103680 A1    Apr. 23, 2009

Related U.S. Application Data

(60) Provisional application No. 60/980,870, filed on Oct. 18, 2007, provisional application No. 60/980,881, filed on Oct. 18, 2007, provisional application No. 60/980,878, filed on Oct. 18, 2007, provisional application No. 60/980,871, filed on Oct. 18, 2007, provisional application No. 60/980,876, filed on Oct. 18, 2007, provisional application No. 60/980,880, filed on Oct. 18, 2007.

(51) Int. Cl.
*G01N 23/20* (2006.01)
(52) U.S. Cl. .......................................... 378/71; 378/73
(58) Field of Classification Search .............. 378/70–90
See application file for complete search history.

(56) References Cited

U.S. PATENT DOCUMENTS

| 2007/0168130 A1 | 7/2007 | Sherwood et al. .............. 702/1 |
| 2007/0222034 A1 | 9/2007 | Park et al. ................... 257/616 |

*Primary Examiner*—Courtney Thomas
(74) *Attorney, Agent, or Firm*—Linda B. Blackburn; Helen M. Galus (57) ABSTRACT

A method provides X-ray diffraction data suitable for integral detection of a twin defect in a strained or lattice-matched epitaxial material made from components having crystal structures having symmetry belonging to different space groups. The material is mounted in an X-ray diffraction (XRD) system. In one embodiment, the XRD system's goniometer angle $\Omega$ is set equal to $(\theta_B - \beta)$ where $\theta_B$ is a Bragg angle for a designated crystal plane of the alloy that is disposed at a non-perpendicular orientation with respect to the {111} crystal plane, and $\beta$ is the angle between the designated crystal plane and a {111} crystal plane of one of the epitaxial components. The XRD system's detector angle is set equal to $(\theta_B + \beta)$. The material can be rotated through an angle of azimuthal rotation $\phi$ about the axis aligned with the material. Using the detector, the intensity of the X-ray diffraction is recorded at least at the angle at which the twin defect occurs.

45 Claims, 10 Drawing Sheets

METHOD OF GENERATING X-RAY DIFFRACTION DATA FOR INTEGRAL DETECTION OF TWIN DEFECTS IN SUPER-HETERO-EPITAXIAL MATERIALS

CROSS-REFERENCE TO RELATED APPLICATIONS

This application claims the benefit of the respective filing dates of, and incorporates by reference the entire respective disclosures of, the following commonly assigned U.S. Provisional Patent Applications: Ser. No. 60/980,870 filed on Oct. 18, 2007, Ser. No. 60/980,881 filed on Oct. 18, 2007, Ser. No. 60/980,878 filed on Oct. 18, 2007, Ser. No. 60/980,880 filed on Oct. 18, 2007, Ser. No. 60/980,876 filed on Oct. 18, 2007, and Ser. No. 60/980,871 filed on Oct. 18, 2007, each of which contains an overlap of inventive entity with the present application. In addition, this application incorporates by reference the entire disclosures of the following commonly assigned nonprovisional U.S. patent applications being filed on the same date as the present application: Ser. No. 12/254,017, entitled "EPITAXIAL GROWTH OF CUBIC CRYSTALLINE SEMICONDUCTOR ALLOYS ON BASAL PLANE OF TRIGONAL OR HEXAGONAL CRYSTAL; Ser. No. 12/254,134, entitled "HYBRID BANDGAP ENGINEERING FOR SUPER-HETERO-EPITAXIAL SEMICONDUCTOR MATERIALS, AND PRODUCTS THEREOF; Ser. No. 12/288,379, entitled "RHOMBOHEDRAL CUBIC SEMICONDUCTOR MATERIALS ON TRIGONAL SUBSTRATE WITH SINGLE CRYSTAL PROPERTIES AND DEVICES BASED ON SUCH MATERIALS; Ser. No. 12/288,380, entitled "X-RAY DIFFRACTION WAFER MAPPING METHOD FOR RHOMBOHEDRAL SUPER-HETERO-EPITAXY; and Ser. No. 12/254,016, entitled "THERMOELECTRIC MATERIALS AND DEVICES; each one claiming priority to the above-cited provisional applications.

ORIGIN OF THE INVENTION

The invention was made in part by employees of the United States Government and may be manufactured and used by or for the Government of the United States of America for governmental purposes without the payment of any royalties thereon or therefor.

BACKGROUND OF THE INVENTION

1. Field of the Invention

The present invention relates to defect detection in semiconductor alloys. More specifically, the invention is a method of generating X-ray diffraction data for use in the detection of twin defects in "super-hetero-epitaxial" materials (materials in which one material having a first crystal structure is epitaxially grown on a different material having a different crystal structure).

2. Description of the Related Art

Cubic semiconductor alloys including group IV elements (i.e., alloy made with carbon (C), silicon (Si), germanium (Ge), and tin (Sn)) in diamond structure; group III-V elements such as GaAs, AlAs, InAs, GaP, AlP, and InP in cubic zincblende structure; and group II-VI elements such as ZnSe, CdS, and HgTe in cubic zincblende structure are important semiconductor materials used in a wide range of devices, such as Field Effect Transistors (FETs), High Electron Mobility Transistors (HEMTS), Hetero Bi-polar Transistors (HBTs), ThermoElectric (TE) devices, photovoltaic solar cells, and photon detectors.

Typically, such alloys, for example, Silicon Germanium (SiGe), are grown on common silicon wafer substrates. However, the growth of thick (i.e., greater than tens of nanometers), high-quality (i.e., defect free) SiGe layers on a silicon substrate is difficult to achieve because SiGe has a larger lattice constant than silicon. This means that the SiGe layers close to the silicon substrate are strained, and severe defects (e.g., threading dislocations, twin defects such as bulk twin domain and micro-twin defects, cracks, delaminations, etc.) develop in the layers of SiGe that exceed a critical thickness of hundreds of nanometers, because of the lattice mismatch. Thus, at best, only strained SiGe layers with very thin thicknesses (i.e., less than hundreds of nanometers) are utilized for high-quality electronic device fabrication. Similar results are observed for other material combinations.

In our commonly filed patent applications referenced above, which have been incorporated into this disclosure by reference, we describe a number of methods for making a broad range of super-hetero-epitaxial materials. For example, such materials may include new group IV, group III-V, group II-VI and other semiconductor alloys aligned in the [111] direction, on substrates with crystal structures having trigonal or hexagonal space group symmetry, As will be explained later in this disclosure, other useful super-hetero-epitaxial combinations are possible as well.

While such methods can yield high-quality, either strained or lattice-matched semiconductor alloys based on a wide variety of selected materials and substrates, problems can develop during fabrication that can affect the quality of the fabricated material. For example, twin defects can be formed in such materials by one or both of (i) double position defects due to crystal structure differences between the epilayer and substrate, and (ii) stacking faults during epilayer growth. Therefore, to examine and/or assure the quality of the resulting rhombohedrally aligned material, it is necessary to check the alloy for both bulk twin domain and micro-twin defects.

Currently, twin defect detection is accomplished by a "transmission electron microscopy" (TEM) analysis. However, TEM results in destruction of the material and is, therefore, only suitable for microscopic laboratory analysis or as a periodic or random sampling check on semiconductor materials being mass-produced. This method is therefore not suitable for generating data for quality control during the fabrication of semiconductor wafers.

Accordingly, for purposes of development of materials and devices to take advantage of the technologies disclosed in our commonly-filed disclosures listed above regarding rhombohedral growth of both strained and lattice-matched cubic semiconductor alloys of a range of group IV, group III-V, group II-VI and other materials on the c-plane of trigonal substrates, as well as numerous materials based on other super-hetero-epitaxial combinations, there is a great need for a nondestructive method for detecting, and generating data regarding, twin defects in such materials.

SUMMARY OF THE INVENTION

It is an object of the present invention to provide a method of generating data indicative of twin defects present in super-hetero-epitaxial materials, including rhombohedrally-grown, strained or lattice-matched cubic semiconductor alloys on the c-plane of trigonal crystals, and other super-hetero-epitaxial materials.

Another object of the present invention is to provide a nondestructive method of generating data indicative of twin defects present in rhombohedrally-grown, strained or lattice-matched cubic semiconductor alloys on the c-plane of trigonal crystal, and other super-hetero-epitaxial materials, where the data can be used for quality control in the production of semiconductor wafers.

In one embodiment, a method is provided to generate X-ray diffraction data suitable for twin defect detection in super-hetero-epitaxial materials, including a strained or lattice-matched cubic semiconductor alloy rhombohedrally grown on a basal plane of a trigonal substrate, or other super-hetero-epitaxial combination.

In one embodiment, an epitaxial layer of a cubic semiconductor alloy is grown on a trigonal substrate, such that the alloy has a {111} crystal plane aligned to a basal plane of the trigonal or hexagonal substrate. The alloy is mounted in an X-ray diffraction (XRD) system having a sample holder with a reference orientation defined thereby such that, when the alloy is positioned in the sample holder, a [111] vector normal to the {111} crystal plane is aligned with the reference orientation. Generally, the XRD system will be capable of rotating the alloy about an axis aligned with the [111] vector. The XRD system also has (i) an X-ray source for generating an X-ray beam that can impinge on the alloy at a goniometer angle $\Omega$, and (ii) a detector having a focused direction for detecting X-ray diffraction therealong at a detector angle measured with respect to the X-ray beam. In the basic single detector XRD system, the X-ray beam and the focused direction reside in a common plane.

At least one of the sample holder, alloy, X-ray source and detector is manipulated such that (i) the goniometer angle $\Omega$ is equal to $(\theta_B-\beta)$ where $\theta_B$ is a Bragg angle for a designated crystal plane of the alloy that is disposed at a non-perpendicular orientation with respect to the (111) crystal plane, and $\beta$ is the angle between the designated crystal plane and the alloy's {111} crystal plane, and (ii) the detector angle is equal to $(\theta_B+\beta)$.

With the alloy so-positioned, the alloy can be rotated through an angle of azimuthal rotation $\phi$ about the axis aligned with the [111] vector as the X-ray beam impinges on the alloy, such that X-ray diffraction is generated for at least one angle of azimuthal rotation at which X-ray diffraction of a twin defect occurs. Using the detector, the intensity of the X-ray diffraction is recorded. Rotation of the alloy may not be required in XRD systems having multiple detectors or multiple X-ray sources. Other embodiments having different positioning settings are also disclosed.

We have determined that the X-ray diffraction method described herein is effective for materials having the following super-hetero-expitaxial combinations of crystalline space symmetries for the constituent materials: cubic on trigonal, trigonal on cubic, hexagonal on trigonal, and hexagonal on cubic.

Other aspects and advantages of the invention will be apparent from the accompanying drawings, and the detailed description that follows.

BRIEF DESCRIPTION OF THE DRAWINGS

For a more complete understanding of the present invention and the advantages thereof, reference is now made to the following description taken in conjunction with the accompanying drawings, wherein like reference numerals represent like parts, in which.

DETAILED DESCRIPTION OF PREFERRED EMBODIMENTS

The following is a detailed description of certain embodiments of the invention chosen to provide illustrative examples of how it may preferably be implemented. The scope of the invention is not limited to the specific embodiments described, nor is it limited by any specific implementation, composition, embodiment or characterization depicted in the accompanying drawings or stated or described in the invention summary or the abstract. In addition, it should be noted that this disclosure describes a number of methods that each comprise a plurality of steps. Nothing contained in this written description should be understood to imply any necessary order of steps in such methods, other than as specified by express claim language.

In the ensuing description, the well-known Miller indices notation of lattice planes is used. That is, crystal planes are designated by numbers within "( )", groups of similar planes are designated by numbers within "{ }", direction or length is designated by numbers within "[ ]", and groups of similar directions are designated by numbers within "< >".

The present invention provides a non-destructive method of generating data that can be used to evaluate twin defects in a high-quality strained or lattice-matched cubic semiconductor layer of certain super-hetero-expitaxial materials. One class of such materials comprises group IV semiconductor materials grown with a {111} crystal plane thereof aligned with and strained or lattice-matched to a basal plane of a trigonal substrate. As will be explained, the invention is operable for other classes of super-hetero-epitaxial materials as well. Other commonly filed patent applications that have been incorporated herein by reference, e.g., application Ser.

No. 12/254,134, entitled "Hybrid Bandgap Engineering for Super-Hetero-Epitaxial Semiconductor Materials, and Products Thereof" (the "Hybrid Bandgap Engineering Disclosure"), address how to formulate and fabricate such other super-hetero-epitaxial materials. The present invention can be used to generate X-ray diffraction data for any of the identified super-hetero-epitaxial combinations, including without limitation [111] oriented, aligned and strained or lattice-matched group IV, III-V, and II-VI alloys of a cubic semiconductor materials (e.g., Si, Ge, Diamond, Sn, GaAs, ZnTe, InP, Zincblendes, etc. and alloys thereof) grown on a trigonal substrate which belongs to a trigonal space symmetry group (e.g., Sapphire, Dolomite, Calcite, etc.); trigonal materials on cubic substrate; materials having crystal structure belonging to a hexagonal space symmetry group (GaN, AlN, Wurtzites) on cubic substrates, and hexagonal materials on trigonal substrates.

Briefly, the fabrication method used herein as an example involves a rhombohedral transformation of lattice parameters to provide for a coincidence lattice between a {111} crystal plane of the cubic diamond SiGe and a {0001} basal plane (i.e., c-plane) of the single crystalline trigonal substrate (e.g., sapphire) during growth of the cubic diamond structure on the substrate. This type of epitaxial growth will also be referred to hereinafter as "rhombohedral growth." As stated above, these methods are valid for a broad range of super-hetero-epitaxial materials, and can be adapted in accordance with the disclosures of our commonly filed patent applications and/or by variations that will be apparent to one of ordinary skill in the art.

The exemplary SiGe semiconductor alloy and then fabrication thereof that will be used for purposes of describing the present invention, is discussed in more detail in our commonly filed application Ser. No. 12/288,379, entitled "Rhombohedral Cubic Semiconductor Materials on Trigonal Substrate with Single Crystal Properties and Devices Base on Such Materials" (the "Rhombohedral Cubic Semiconductor Disclosure"). This alloy fabrication involves growing a cubic diamond structure SiGe on a trigonal crystal structure of single crystalline aluminum oxide ($Al_2O_3$) sapphire referred to hereinafter as "single crystalline $Al_2O_3$". The goal of reduced or zero defect/dislocations in this SiGe semiconductor alloy is achieved by arranging for a coincidence lattice between the cubic diamond structure SiGe and the single crystalline $Al_2O_3$. In order to explain the lattice alignment, reference will now be made to FIGS. 1A, 1B, 2A, and 2B.

Figure 01A:
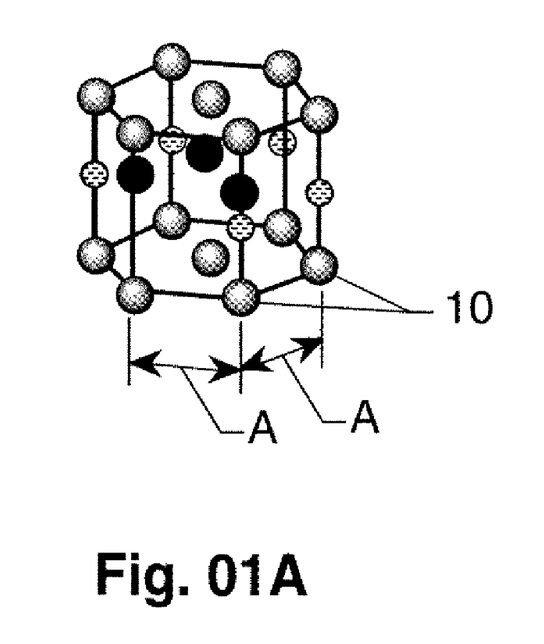
FIG. 1 comprises simplified views of an exemplary substrate material, sapphire, for super-hetero-epitaxy.
FIG. 1A depicts a simplified view of the atomic structure of single crystalline sapphire (aluminum oxide, $Al_2O_3$)
FIG. 1B depicts a simplified planar view of the {0001} c-plane of the lattice of single crystalline $Al_2O_3$.
Figure 01B:
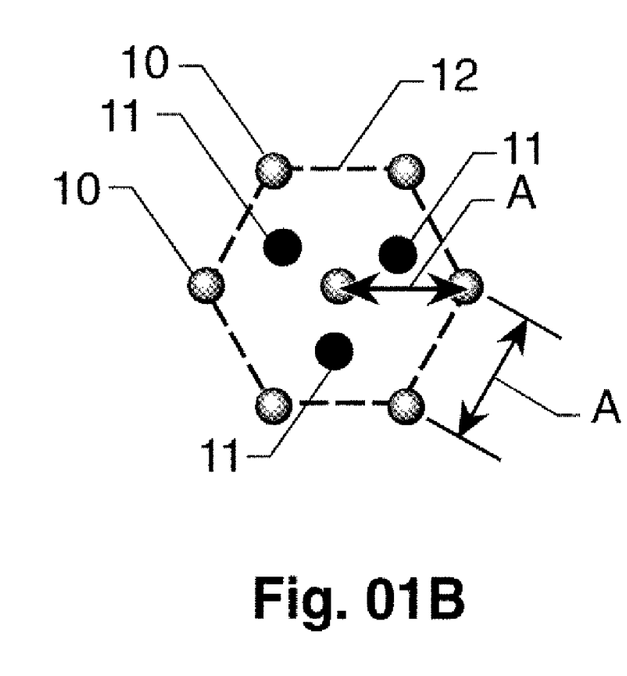

In FIG. 1A, a simplified view of the atomic structure of single crystalline $Al_2O_3$ is illustrated, with the basal plane's lattice constant (i.e., atomic distance) denoted by the letter "A". The actual three-dimensional atomic structure of sapphire is very complex, but it has the same threefold symmetry as the simplified model in FIG. 1A. For single crystalline $Al_2O_3$, A is equal to 4.7580 angstroms. A trigonal structure of the {0001} c-plane (i.e., one of the group of two similar planes) of single crystalline $Al_2O_3$ is illustrated in FIG. 1B, where the grey shaded circles 10 represent crystal lattice points in the {0001} c-plane and the black shaded circles 11 represent trigonal symmetry of the structure beneath the {0001} c-plane. The trigonal relationship with crystal lattice points 10 at the vertices thereof is referenced by numeral 12 and defines the <1, 0, −1, 0> orientation of the {0001} c-plane. The <1, 0, −1, 0> orientation refers to the group of three directions corresponding to the three similar planes defined by the {0001} c-plane.

As is known in the art and for purposes of the present invention, the term "{0001} c-plane" refers to single crystalline $Al_2O_3$ that has been perfectly cut along the {0001} c-plane as well as slightly miscut single crystalline $Al_2O_3$ where "slightly miscut" refers to cut angles of ±10° or less. Methods of cutting single crystalline $Al_2O_3$ to expose the perfect or miscut {0001} c-plane thereof are well known in the art.

Figure 02A:
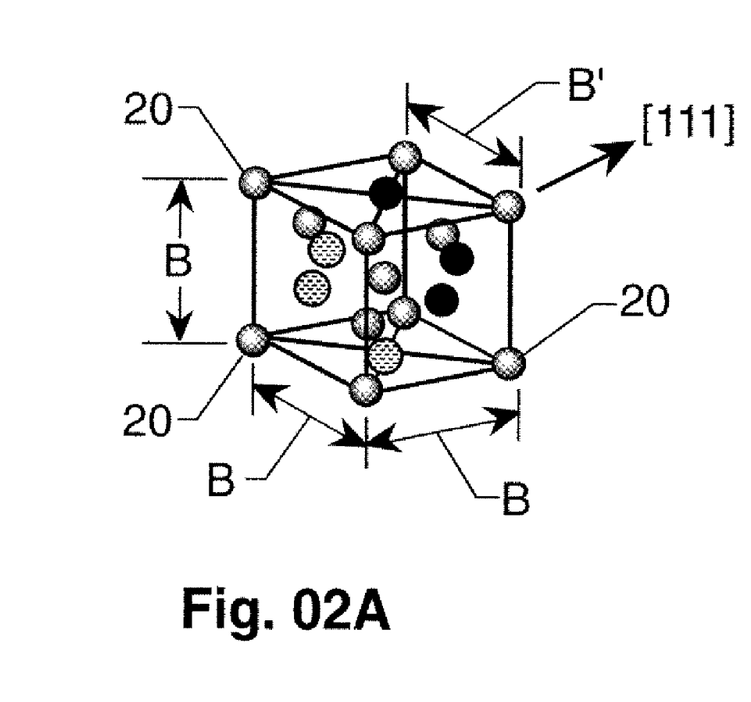
FIG. 2 comprises views of an exemplary cubic crystal structure as may be used in super-hetero-epitaxy.
FIG. 2A depicts the cubic diamond atomic structure of a group IV element.
FIG. 2B depicts an atomic, planar view of the {111} crystal plane of the cubic structure of FIG. 2A.
Figure 02B:
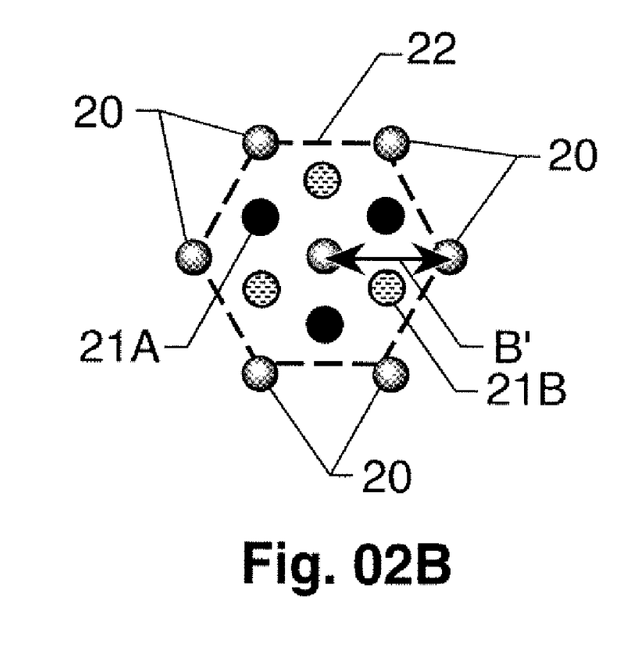

In FIG. 2A, the cubic diamond atomic structure of a group IV element is illustrated with a side dimension lattice constant (i.e., atomic distance between atoms 20) of "B" and the atomic distance (between center to corner atoms) of B' (i.e., the <220> distance) in the {111} crystal plane of the cubic diamond structure. (Cubic zincblende structure of group III-V and II-VI has similar structure with two different atoms.)

FIG. 2B depicts a planar view of the {111} crystal plane of the cubic diamond structure, where the grey shaded circles represent atoms 20 in the {111} crystal plane and the differently shaded circles represent atoms 21A and 21B on multiple layers of the structure beneath the {111} crystal plane.

Lattice matching is addressed in detail in our commonly filed patent application Ser. No. 12/254,017, entitled "Epitaxial Growth of Cubic Crystalline Semiconductor Alloys on Basal Plane of Trigonal or Hexagonal Crystal" (the "Lattice Matching Disclosure"), as well as our Hybrid Bandgap Engineering Disclosure. One possible coincidence lattice alignment with respect to the present SiGe example is that the hexagonal arrangement with atoms 20 at the vertices thereof as referenced by numeral 22 defines the <110> orientation of the {111} crystal plane. In this arrangement, the relationship between B and B' in the cubic diamond structure is $B'=B(\sqrt{3}/2)$. For a SiGe alloy having a cubic diamond structure, the value for B (and, therefore B') is dependent on the composition of the alloy. That is, for the general $Si_{1-z}Ge_z$ alloy with germanium composition Z in atomic percent, the lattice constant $B_{SiGe}$ is defined by $$ZB_{Ge}+(1-Z)B_{Si}$$

where $B_{Ge}$ is the side dimension lattice constant of germanium (i.e., 5.65791 angstroms), and $B_{Si}$ is the side dimension lattice constant of silicon (i.e., 5.43107 angstroms). (The accuracy of the lattice constant calculation can be improved by including a bowing parameter as is known in the art.) More complex examples are addressed in the Lattice Matching and Hybrid Bandgap Engineering Disclosures.

Applying the above relationships, $B_{SiGe}$ is equal to approximately 5.49406 angstroms, and the lattice constant $B'_{SiGe}$ in the {111} crystal plane of the cubic diamond structure SiGe is equal to approximately 4.7580 angstroms when Z=0.2777. This is one of the possible azimuthal, i.e. in-plane, atomic alignments in which SiGe[111] and sapphire [0001] are in the same direction. Other azimuthal alignments are also possible while SiGe[111] and sapphire [0001] are still in the same direction. The described twin detection XRD method can be applied to all azimuthal alignment cases as long as cubic [111] direction is aligned with trigonal [0001] direction.

Thus, high quality SiGe growth can be achieved by a rhombohedral epitaxy technique that defines the (i) plane and orientation relationships between cubic diamond SiGe and the $Al_2O_3$ substrate, and (ii) the composition of the cubic diamond SiGe. For rhombohedrally grown SiGe on single crystalline $Al_2O_3$, the {111} crystal plane of cubic diamond SiGe is grown on the {0001} c-plane of single crystalline $Al_2O_3$. In one azimuthal alignment, growth is controlled such that the <110> orientation of cubic diamond SiGe is aligned (i.e., parallel to) with the <1, 0, −1, 0> orientation of the {0001} c-plane. Other azimuthal alignments are also possible while SiGe[111] and sapphire [0001] are still in the same direction. The described twin detection XRD method can be applied to all azimuthal alignment cases as long as cubic [111] direction is aligned with trigonal [0001] direction (as well as to other super-hetero-epitaxial cases as discussed below).

The above described in-plane/orientation alignment can achieve a lattice match when the cubic diamond SiGe, having a general composition defined by $Si_{1-Z}Ge_Z$, has a germanium composition of 0.2777 atomic percent and a silicon composition of 0.7223 atomic percent. At this composition, the lattice constant $B'_{SiGe}$ is given by $$(sqrt(3)/2)*(ZB_{Ge}+(1-Z)B_{Si})$$

which equates to 4.7580 angstroms for Z=0.2777, thereby matching the lattice constant A of single crystalline Al2O3. Therefore, by what amounts to a rhombohedral transformation of lattice parameters, lattice matched condition or strained condition between cubic diamond SiGe and the single crystalline trigonal $Al_2O_3$, can thereby be achieved during the growth process. In general, the lattice matched growth and strained growth for such "rhombohedrally grown" cubic semiconductor alloys will allow a high-quality semiconductor alloy layer to be grown for use in a wide variety of electronic devices.

Figure 03:
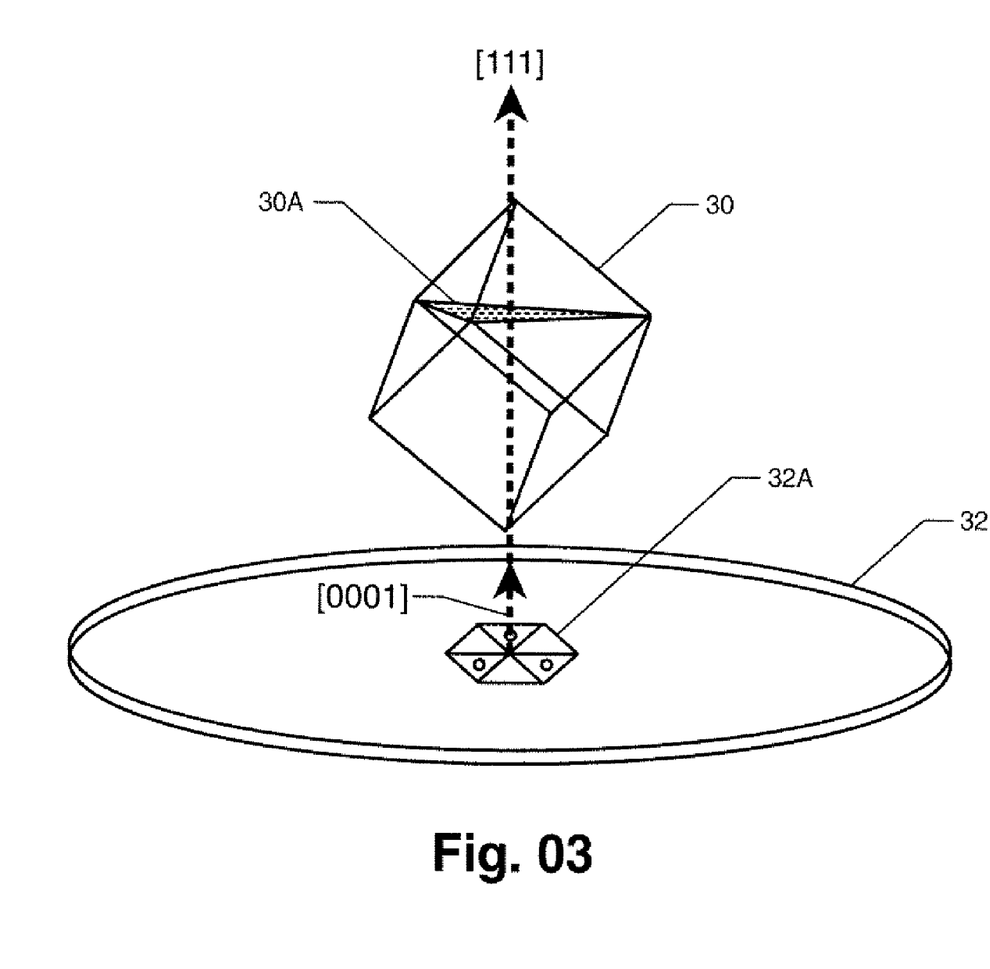
FIG. 3 is a diagrammatic view of the orientation of a rhombohedrally grown cubic structure semiconductor alloy on a trigonal substrate.

The above-described fabrication process can be extended, by way of further example, to group IV, group III-V, and group II-VI alloys that are similarly oriented/aligned for epitaxial growth on a {0001} basal plane of a trigonal substrate. This is depicted diagrammatically in FIG. 3 where a (111) crystal plane 30A of a cubic semiconductor alloy structure 30 is aligned and strained or lattice-matched to the {0001} plane 32A of a trigonal substrate 32. Note that the corresponding [111] and [0001] vectors (i.e., normal to the respective crystal planes) are also illustrated. When epitaxial growth occurs with this result, structure 30 is said to be "rhombohedrally grown" on substrate 32. (Other super-hetero-epitaxial possibilities will be discussed below.)

The above-described alloy fabrication can be achieved in a variety of ways. The trigonal substrate can be obtained commercially or manufactured. The substrate would typically be cleaned and/or etched before growth of the cubic diamond semiconductor alloy thereon. Rhombohedrally aligned, strained or lattice-matched layer(s) can be grown with various standard growth methods, including but not limited to, Molecular Beam Epitaxy (MBE), Metal-Organic Chemical Vapor Deposition (MOCVD), MetalOrganic Chemical Vapor Phase Epitaxy (MOVPE), Hydride Vapor Phase Deposition (HVPE), Liquid Phase Epitaxy (LPE), Physical Vapor Deposition (PVD), Pulsed Laser Deposition (PLD), and sputtering methods.

To fabricate the final device structures, standard microfabrication technologies can be used, including but not limited to, lithography, etching, metallization, dopant diffusion/implantation and oxidation. The resulting cubic diamond semiconductor alloy on the trigonal substrate can be used "as is" or can be removed from the substrate after growth to a desired thickness. Such methods of removal are well known in the art and could include laser cutting, hydrogen cracking, etc., the choice of which is not a limitation of the present invention.

Figure 04:
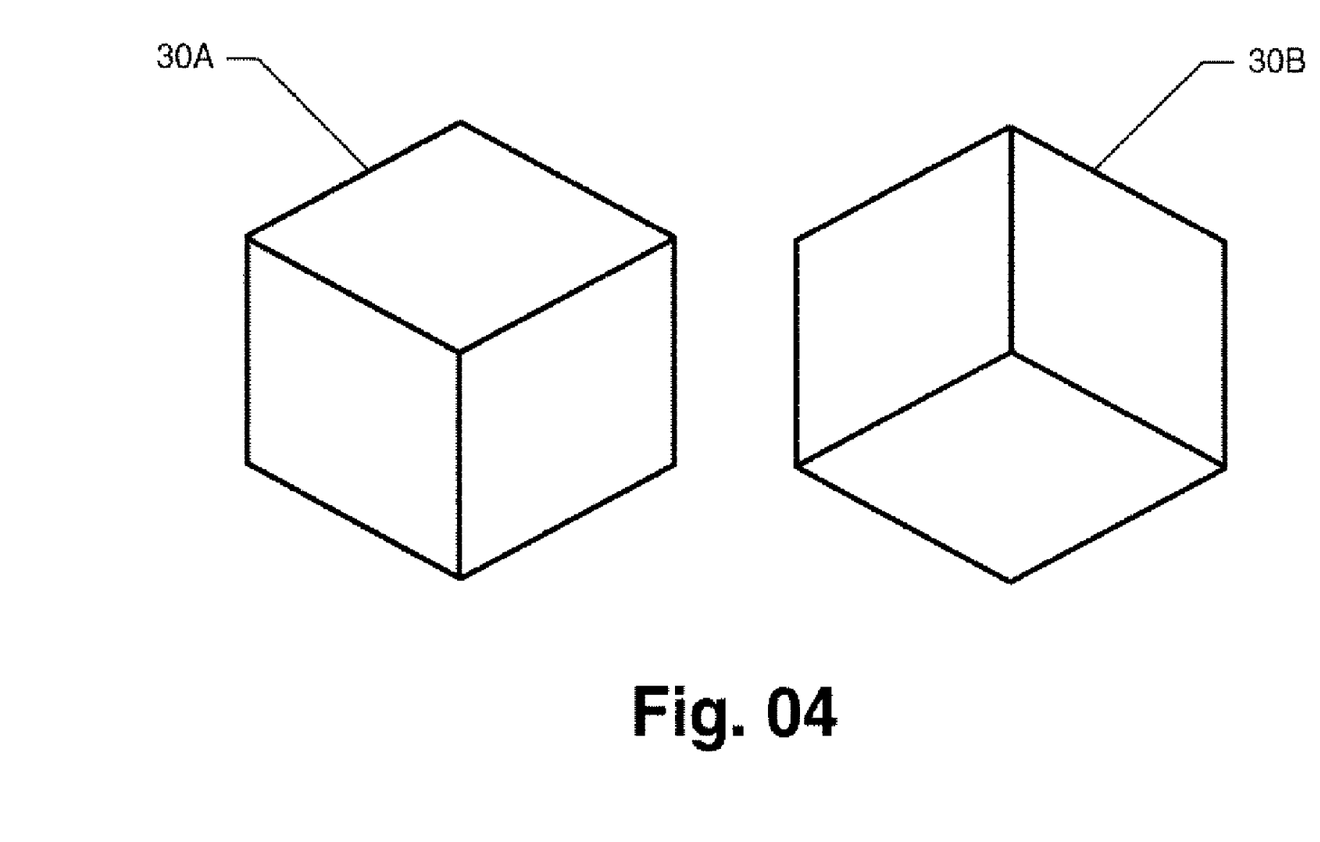
FIG. 4 is a diagrammatic view of two cubic structures viewed from a <111> direction thereof where one represents a single crystalline cubic alloy and the other represents a twin defect.

As with any semiconductor material fabrication process, problems that affect the quality of the finished product can develop. For example, the quality of rhombohedrally-grown and lattice-matched or strained cubic semiconductor alloy is degraded by the presence of twin defects. A twin defect for this type of alloy is illustrated in FIG. 4 where two cubic structures 30A and 30B are shown as they would be viewed from a <111> orientation. A twin defect is indicated when structures 30A and 30B are rotated with respect to one another. When this occurs, the trigonal symmetry of the substrate material can provide less formation energy to one structure (e.g., structure 30A) and greater formation energy to the other structure (e.g., structure 30B). Therefore, a high-quality crystalline material can be grown when there are few or no twin defects.

The rhombohedrally-grown, lattice-matched or strained cubic semiconductor alloy can be evaluated for twin defects using data generated by a non-destructive data collection method in accordance with the present invention. Since the method is non-destructive, the present invention can be readily adapted for use in mass production of the above-described rhombohedrally-grown, lattice-matched or strained cubic semiconductor alloys. For example, the present invention could be incorporated into a manufacturing process to either aid in the optimization of growth parameters or as a means for quality monitoring and quality control of the finished products (e.g., semiconductor wafers).

The present invention provides a method of generating X-ray diffraction (XRD) data that can then be used to quantitatively estimate twin defect concentration in a lattice-matched or strained cubic semiconductor alloy that has been rhombohedrally grown on a basal plane of trigonal substrate, as well as in other super-hetero-epitaxial combinations, as will be discussed. In an exemplary case this could be a material wherein a {111} crystal plane of the cubic semiconductor alloy is aligned with and strained or lattice-matched to the trigonal substrate's basal plane. The method uses a conventional X-ray diffraction (XRD) system, the operations of which are well known and understood in the art.

Figure 05:
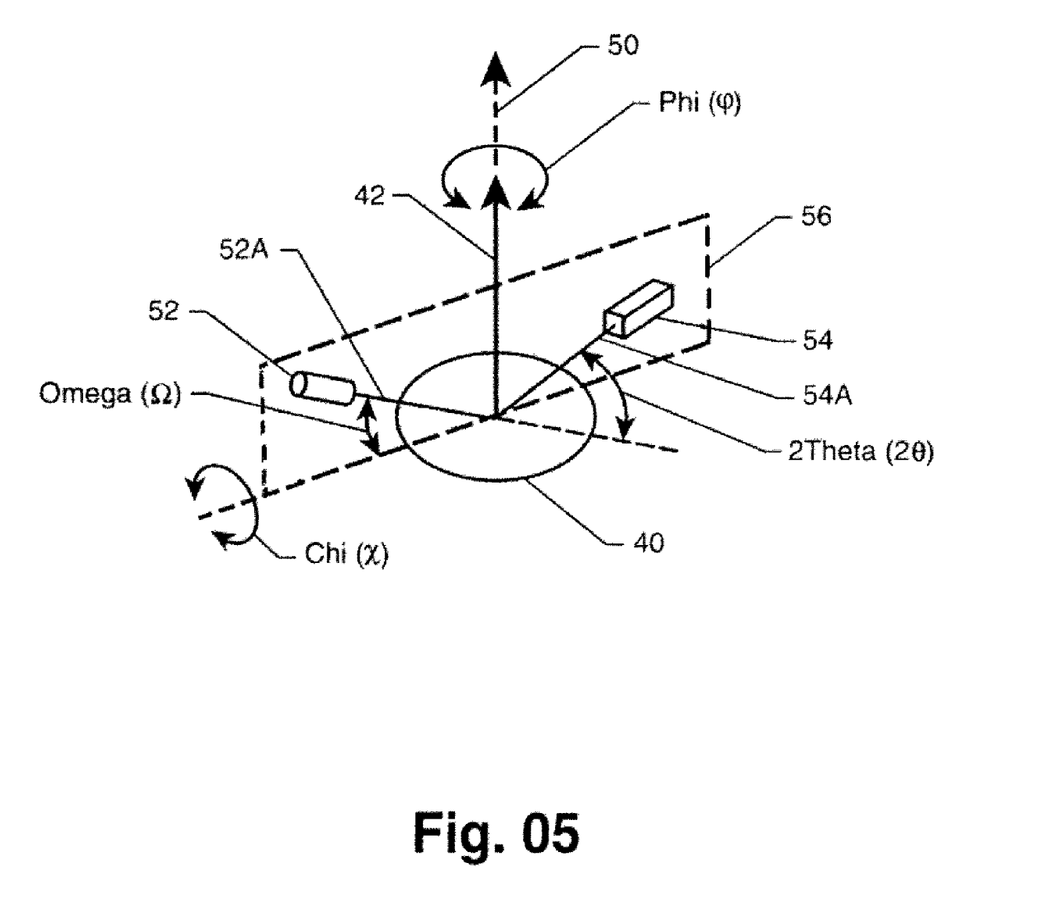
FIG. 5 is a real space diagram illustrating the set-up of a conventional X-ray diffraction (XRD) system.

A brief description of an XRD system will be provided herein to facilitate an understanding of the invention. FIG. 5 illustrates a "real space" view of a conventional XRD system. The XRD system typically includes a sample holder (not shown for sake of clarity) that positions a sample 40 to be tested such that the sample's surface normal 42 is aligned with a reference orientation of the XRD system that is indicated by arrow 50. The XRD system is equipped to rotate sample 40 about normal 42 through angles of azimuthal rotation up to 360° with the angle of rotation being indicated by φ. The XRD system is further equipped to tilt sample 40 relative to reference orientation 50 through a tilt angle χ. The XRD system also includes an X-ray source 52 and an X-ray detector 54. X-ray source 52 produces an X-ray beam 52A that impinges on sample 40 while X-ray detector 54 is sensitive to X-ray diffraction (caused by X-ray beam 52A) along a direction of focus referenced by arrow line 54A. X-ray beam 52A and direction of focus line 54A lie in a common plane indicated by dashed line box 56. The angle Ω that X-ray beam 52A makes with sample 40 will be referred to herein as the goniometer angle. The angle that direction of focus 54A makes with X-ray beam 52A is generally referred to as 2θ for the conventional "θ-2θ" Bragg-Brentano XRD system setup, where θ is the angle that sample 40 makes with X-ray beam 52A.

Three embodiments of the invention are illustrated that define setup and operational parameters for an XRD system that will generate XRD data for a rhombohedrally-grown, strained or lattice-matched cubic semiconductor alloy (or other super-hetero-epitaxial materials as discussed herein). In each embodiment, the Bragg angle must be calculated between the semiconductor alloy's {111} crystal plane and another crystal plane of the alloy that (i) is not perpendicular to the alloy's {111} crystal plane, and (ii) will produce diffraction when impinged by an X-ray. For a cubic semiconductor alloy, the non-perpendicular and diffraction producing crystal planes include the {220}, {440}, {224}, {113}, {004}, {001}, {221}, {223}, {112}, {115}, {116} and {331} crystal planes. In general, the selected crystal plane is selected based on the X-ray diffraction intensity that it will produce.

The Bragg angle $\theta_B$ is calculated using the well known Equation $$\sin(\theta_B)=(n*\lambda*(sqrt(h^2+k^2+l^2)))/(2*L)$$

where
n is an integer that defines the n-th order diffraction peak,
$\lambda$ is the wavelength of X-ray beam 52A,
h, k, l are Miller indices associated with the alloy's crystal plane spacing, and
L is the lattice constant of the alloy.

Figure 06:
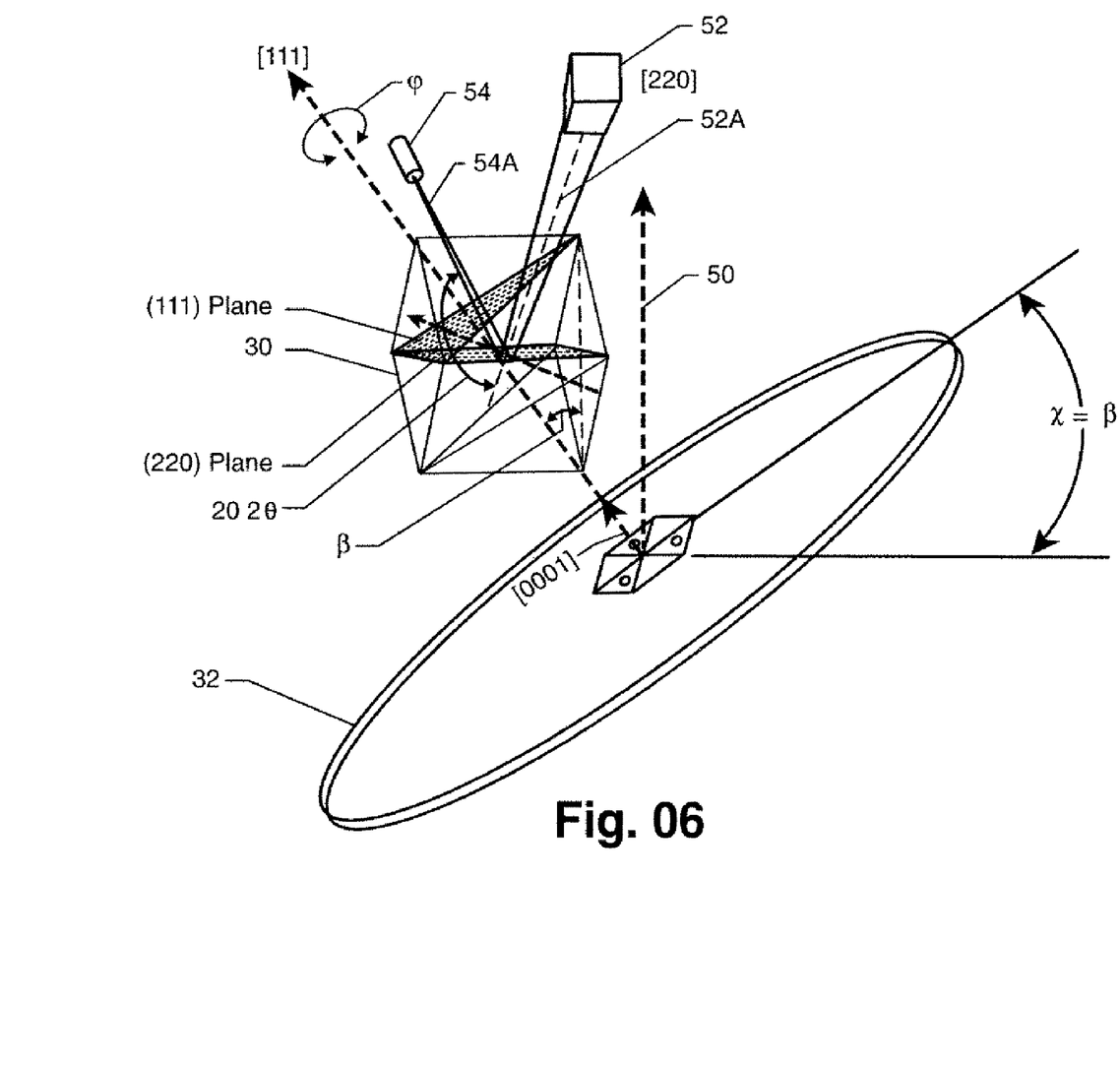
FIG. 6 is a diagrammatic view of the XRD system setup for generating XRD data for a rhombohedrally-grown, strained or lattice-matched cubic semiconductor alloy in accordance with a first embodiment of the present invention.
Figure 07:
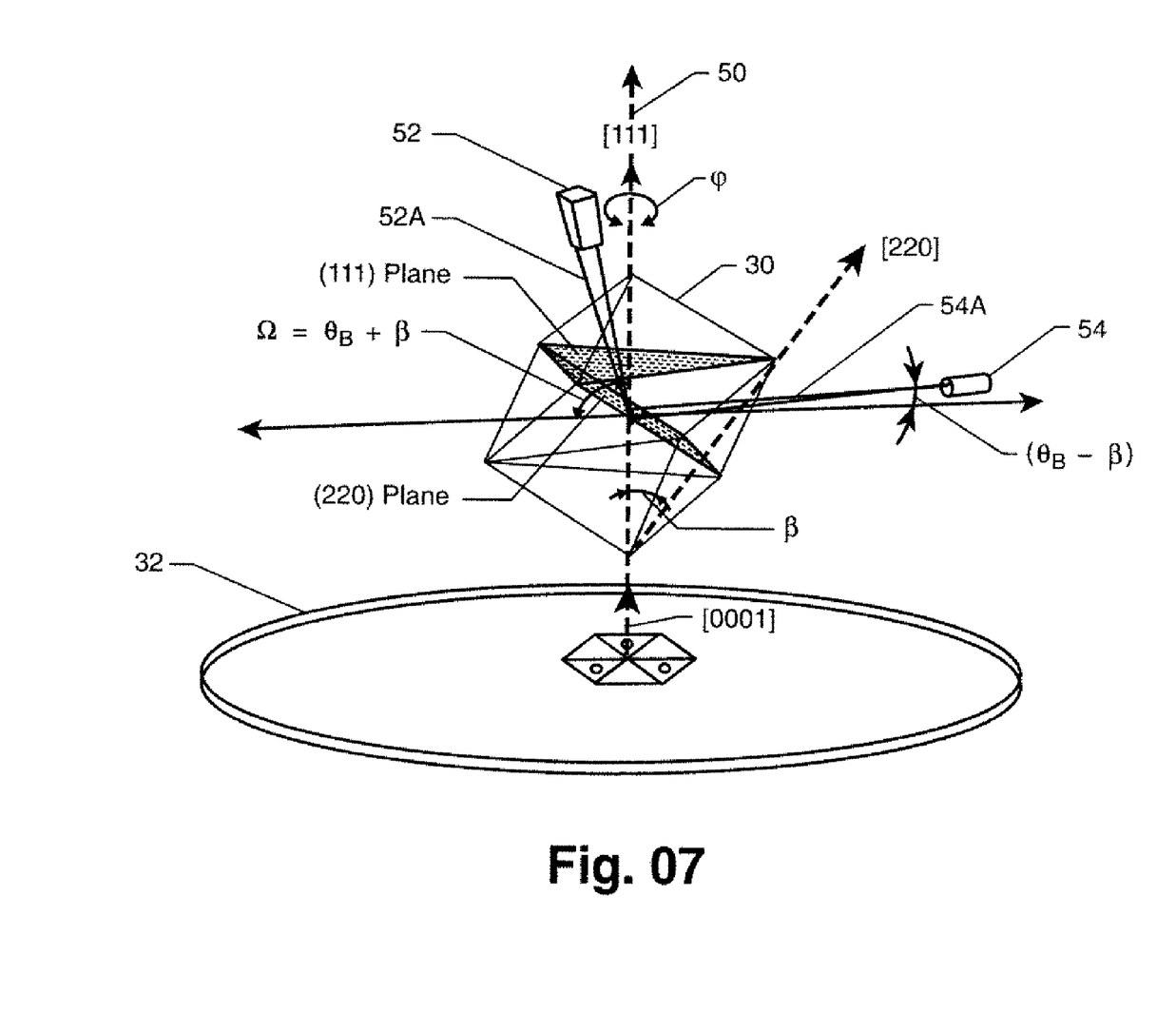
FIG. 7 is a diagrammatic view of the XRD system setup for generating XRD data for a rhombohedrally-grown, strained or lattice-matched cubic semiconductor alloy in accordance with a second embodiment of the present invention.
Figure 08:
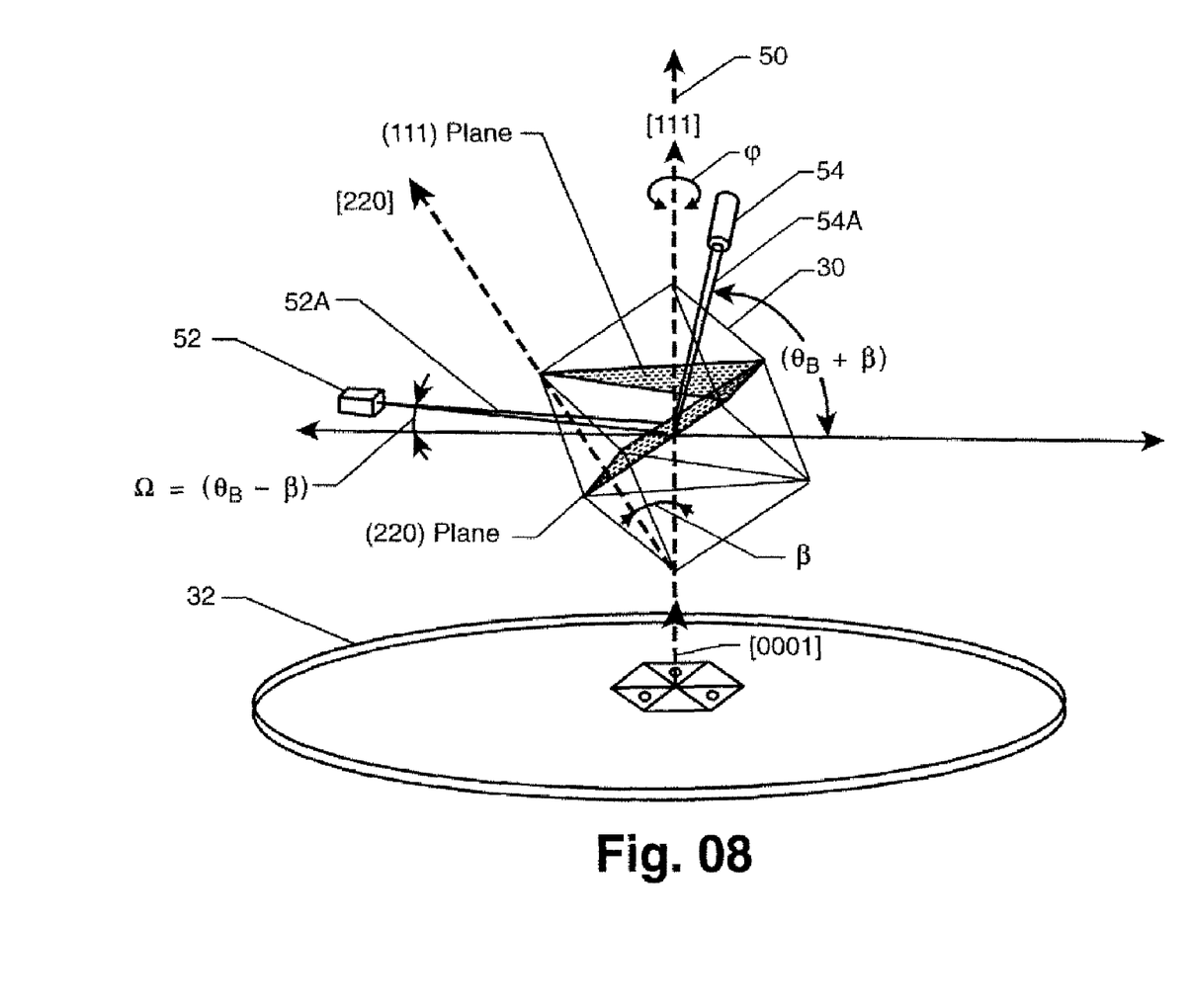
FIG. 8 is a diagrammatic view of the XRD system setup for generating XRD data for a rhombohedrally-grown, strained or lattice-matched cubic semiconductor alloy in accordance with a third embodiment of the present invention.

Reference will now be made to FIGS. 6-8 to aid in the description of the three exemplary embodiments of the present invention. In each of these figures, the reference characters associated with the XRD system described in FIG. 5 are used, the cubic semiconductor alloy structure is indicated by reference numeral 30, and the trigonal substrate on which cubic structure has been rhombohedrally-grown is indicated by reference numeral 32. By way of example, the {220} crystal plane is the selected crystal plane that is non-perpendicular to the alloy's {111} crystal plane. For clarity of illustration, one (220) plane is indicated by crosshatching with its corresponding [220] vector (normal) being illustrated in dashed-line form. Similarly, only one (111) plane is shown with its corresponding [111] vector (normal) illustrated in dashed line form.

In the first embodiment, illustrated in FIG. 6, the following setup criteria apply:
(i) The goniometer angle $\Omega$ associated with X-ray beam 52A is set equal to the Bragg angle $\theta_B$.
(ii) Detector 54 is positioned so that its direction of focus 54A is equal to $2*\theta_B$ (i.e., the conventional Bragg-Brentano setup is used where $\theta=\theta_B$).
(iii) The alloy sample is positioned (e.g., via movement of the XRD system's sample holder) such that the [111] vector of structure 30 (i.e., the [111] vector is normal to the {111} crystal plane) makes an angle of $\chi=\beta$ relative to reference orientation 50 of the XRD system and lying in the common plane defined by X-ray beam 52A and direction of focus 54A.

The angle $\beta$ is the inter-planar angle between the alloy's {111} crystal plane and the selected non-perpendicular plane (i.e., the {220} crystal plane in the illustrated example). As is known in the art, the inter-planar angle ~ between two crystal planes is defined as $$\cos(\beta)=(h_1h_2+k_1k_2+l_1l_2)/sqrt((h_1^2+k_1^2+l_1^2)*(h_2^2+k_2^2+l_2^2))$$

where $(h_1, k_1, l_1)$ and $(h_2, k_2, l_2)$ are the Miller indices associated with the two crystal planes (i.e., the {111} and {220} crystal planes in the illustrated example). For clarity of illustration, the inter-planar angle $\beta$ is shown between the [111] and [220] vectors.

With the above-described test-ready positioning of the alloy, the XRD system is then operated as follows:
(i) X-ray source 52 generates X-ray beam 52A that is impinged on the alloy while detector 54 is activated to record X-ray diffraction.
(ii) As X-ray source 52 and detector 54 are operated, the sample is rotated in the illustrated test-ready position through an angle of azimuthal rotation $\phi$. In this test-ready position, the axis of azimuthal rotation is defined by the [111] vector. This type of XRD system operation is known in the art as a "phiscan."
(iii) The phiscan is carried out until X-ray diffraction is recorded for the selected non-perpendicular crystal plane (i.e., the {220} crystal plane in the illustrated embodiment) and for an azimuthal location/angle where a twin defect can occur. This can be achieved by either analyzing the recorded data peaks or by rotation of the sample with respect to major or minor flats of the sample in order to generate X-ray diffraction of the lattice-matched crystal or twin defect.

X-ray diffraction at these two locations can be assured by providing for a minimum amount of rotation for a given alloy. For example, in terms of SiGe grown as previously-described herein with the selected non-perpendicular crystal plane being the {220} crystal plane, XRD peaks of a twin crystal are 60° off (in the phiscan's plane of rotation) from the lattice-matched dominant crystal's {220} peaks. Accordingly, when the phiscan in this example covers at least 120°, the XRD system will record at least one {220} crystal peak and at least one twin crystal peak. Additional peaks could be recorded by expanding the phiscan to a full 360°.

Figure 09:
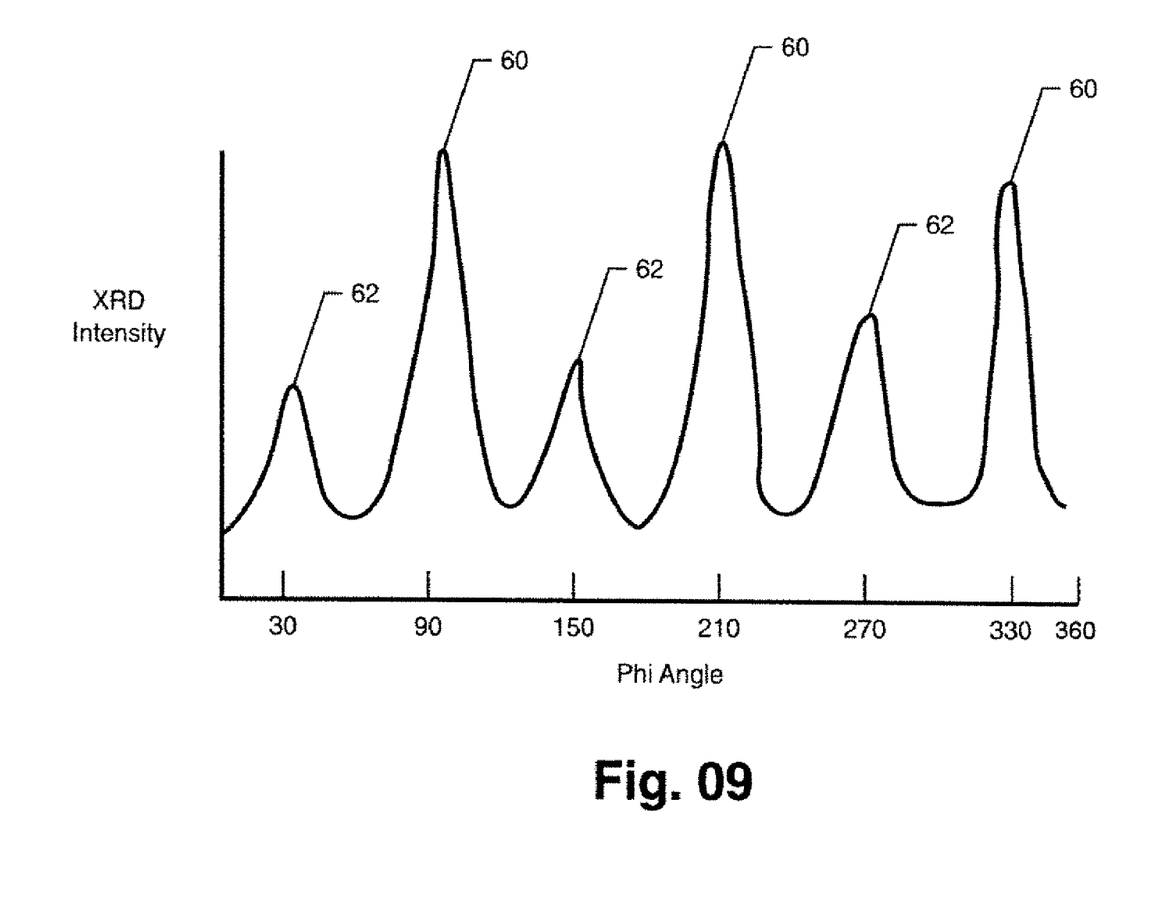
FIG. 9 is a phiscan of XRD intensity of a rhombohedrally grown cubic SiGe alloy on trigonal c-plane of sapphire.

For example, intensity as a function of the angle of azimuthal rotation $\phi$ for the above-described SiGe is shown in FIG. 9 for a full 360° phiscan where lattice-matched {220} crystal peaks are indicated at 60 and twin crystal peaks are indicated at 62. Note the 60° spacing between peaks. Due to the crystals trigonal symmetry, 180° spacing and 300° spacing has the same effect as 60° spacing. In the present invention, rotation of the sample may not be required when using XRD systems having multiple detectors or multiple X-ray sources as the angles between detectors or between X-ray sources can be arranged to have the same effect as sample rotation.

The XRD intensity data generated by the above-described setup and operational parameters can be used to estimate twin defect concentration. Ratios of intensity (i.e., using intensity recorded at two angles of $\phi$) based on either peak height or peak area can be used as both are provided by the present invention. Thus, where the sample is rotated, a rotation of 120° will assure detection of a crystal peak and a twin crystal peak. However, a rotation of only 60° could also achieve the same result depending on the sample's start position relative to the X-ray source/detector. Furthermore, twin defect concentration could also be estimated by just recording intensity data related to a twin defect. Accordingly, it is to be understood that the present invention could also be used to obtain absolute intensity recorded at just one angle of $\phi$ associated with a twin defect. Once again, either peak height or peak area could be used as the measured data.

Second and third test-ready position setups will now be explained with reference to FIGS. 7 and 8. As mentioned above, the first step is to calculate the Bragg angle $\theta_B$ for the alloy that will once again be SiGe for purpose of illustration. In the second embodiment of the present invention illustrated in FIG. 7, the following setup criteria apply:
(i) The goniometer angle $\Omega$ is set equal to $(\theta_B+\beta)$ where $\beta$ is once again the inter-planar angle described above.
(ii) Detector 54 is positioned so that its direction of focus 54A is equal to $(\theta_B-\beta)$
(iii) The sample is positioned such that the [111] vector is aligned with the XRD system's reference orientation 50. That is, the tilt angle $\chi$ equals zero.

With the above-described test-ready positioning of the alloy, the XRD system is then operated as previously described for the first embodiment.

In a third embodiment illustrated in FIG. 8, the Bragg angle $\theta_B$ is calculated and the following setup criteria apply:
(i) The goniometer angle Ω is set equal to $(\theta_B-\beta)$ where β is once again the inter-planar angle described above.
(ii) Detector 54 is positioned so that its direction of focus 54A is equal to $(\theta_B+\beta)$.
(iii) The sample is positioned such that the [111] vector is aligned with the XRD system's reference orientation 50. That is, the tilt angle χ equals zero.

With the above-described test ready positioning of the alloy, the XRD system is then operated as previously described for the first embodiment.

In each of the above-described embodiments, the phrase "phiscan" assumes an azimuthal rotation of the sample being tested. However, the present invention is not so limited. That is, sample rotation may not be required in test set-ups that utilize multiple detectors to record diffraction data at the appropriate angles of φ where these angles lie in a plane that would be defined if the sample were rotated as previously described.

Furthermore, the present invention can be used to generate X-ray diffraction data either when the trigonal substrate has been perfectly cut or slightly miscut or offcut (i.e., cut angles of ±10° or less as was described previously herein). When the substrate has been miscut, the angles associated with the XRD system (i.e., the goniometer angle, detector angle and tilt angle) are simply adjusted by an offset angle that is based on the miscut or offcut angle.

The techniques described above are not limited to group IV alloys. Cubic crystal includes group IV elements in diamond structure, group III-V and II-VI elements in zincblende structure as well as other elements in Body Centered Cubic (BCC) and Face Centered Cubic (FCC) structures. The four lattice matching equations developed in our Lattice Matching Disclosure apply for all these materials. The X-ray diffraction methods of the present invention may be applied on these lattice matching conditions, on group IV, III-V, II-VI semiconductors, and rhombohedrally-lattice-matched FCC and BCC materials on various trigonal substrates. Moreover, the same analysis applies to other crystal combinations as will be discussed below. For those relations for which the above twin detection XRD method works, it can be used to monitor the epitaxial layers as a non-destructive evaluation tool. It can be used for quality control and selection of prime wafers.

Figure 10:
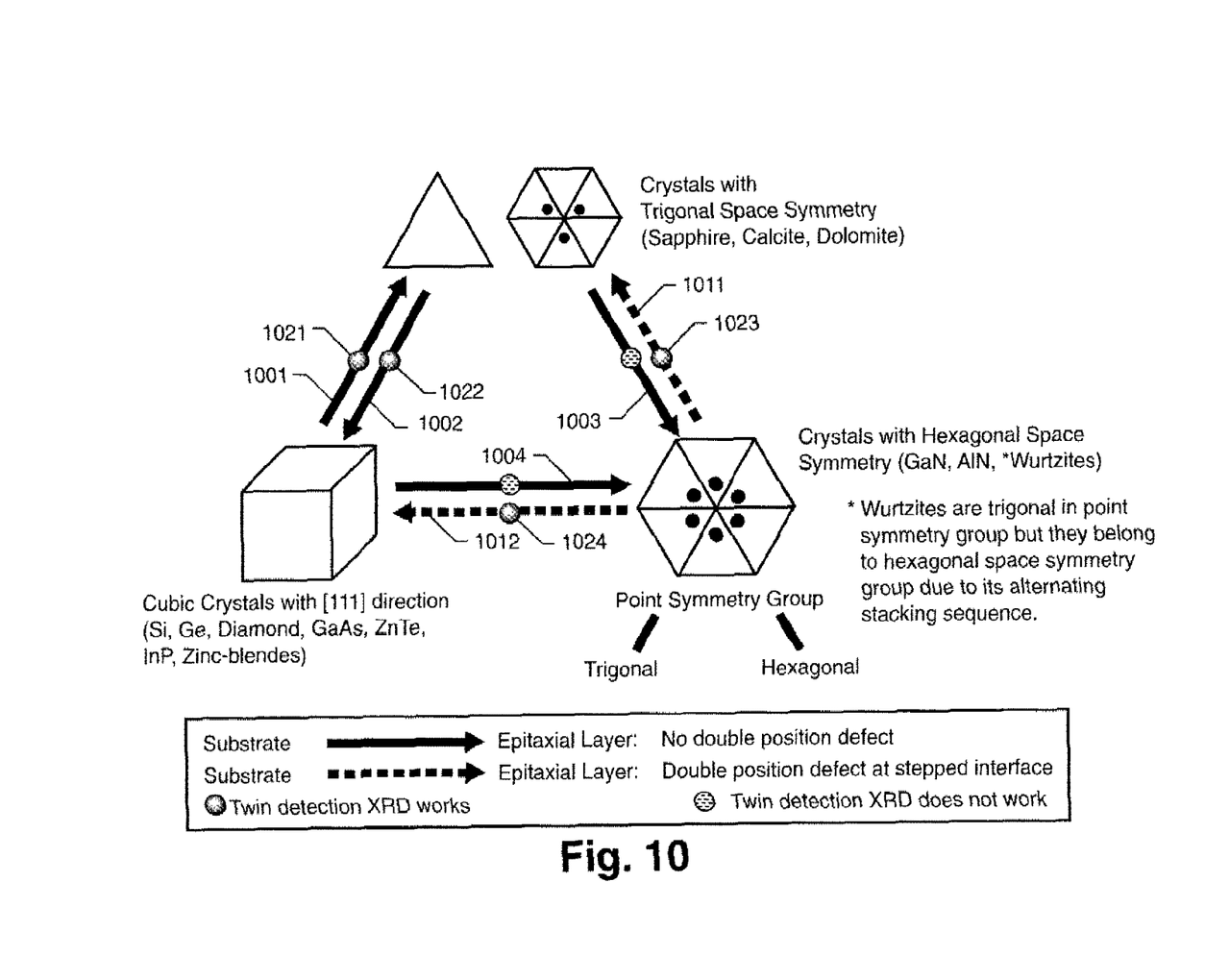
FIG. 10 is a graphic showing Super-Hetero-Epitaxial relationships and validity of twin detection XRD methods for those relationships.

FIG. 10 illustrates what we refer to as the "Tri-Unity Relationship" among materials with crystal structures having symmetry belonging to the cubic, trigonal and hexagonal space groups. Arrows 1001, etc. were drawn from each underlying crystal structure as substrate, to an epitaxial crystal structure. All of three crystal structures satisfy 120° rotational symmetry along cubic [111] or trigonal/hexagonal [0001] axes. However double position defects can occur if the underlying crystal has hexagonal space symmetry including III-N Wurtzite crystal structure, because it has additional 60° rotational space symmetry. The epitaxial growth with inevitable double position defect is drawn in dotted arrows 1011 and 1012. The epitaxial growth combinations marked with solid lines 1001, 1002, 1003, and 1004 can avoid double position defects that make twin crystals. The defect-free (no twin crystal) growth in solid line combinations occurs in certain narrow "golden" growth conditions by utilizing the difference in the formation energy (as explained at greater length in the Rhombohedral Cubic Semiconductor Disclosure).

As for the dotted epitaxial lines 1011 and 1012, in spite of the interfacial double position defect at the interface, we do not exclude a possibility that a single crystalline layer can be formed by internal stacking faults and domain expansion phenomena in which domain size becomes larger than a wafer size. One example of such a domain expansion is the spinodal decomposition.

As for the diatomic and more complex cubic crystals, such as zincblendes (GaAs, AlP, and so on), atomic inversion defect such as Ga—As vs. As—Ga can occur since {111} planes are polarized planes. However the inversion defects will not be considered here because they are more related with specific stacking sequence.

The twin detection XRD methods described above apply to the various epitaxial relations that have filled circles 1021, 1022, 1023, and 1024 in FIG. 10.

Accordingly, application of twin detection XRD methods described herein on the epitaxial systems shown in Table 1 is valid:

TABLE 1

Application of twin detection XRD methods on epitaxial systems (1) <111> Cubic Crystal Layer on {0001} Plane of Trigonal (Space Symmetry) Crystal Material Layer or Substrate
(2) <0001> Trigonal Crystal Layer on {111} Plane of Cubic Crystal Material Layer or Substrate
(3) <111> Cubic Crystal Layer on {0001} Plane of Hexagonal (Space Symmetry) Crystal Material Layer or Substrate
(4) <0001> Trigonal Crystal Layer on {111} Plane of Hexagonal (Space Symmetry) Crystal Material Layer or Substrate The advantages of the present invention are numerous. The XRD data generation method is a powerful non-destructive data generation tool that can be used in both laboratory and manufacturing applications to estimate twin defects in a wide range of super-hetero-epitaxial materials as herein described. In terms of mass production applications, the present invention can be used to define growth parameters that minimize or eliminate twin defects. The method could be integrated into epitaxial growth equipment to provide for iterative growth parameter changes as the need arises. The present invention can be used to verify structures, and could also form the basis of a quality monitoring and quality control system that performed a 100% evaluation of post-production products. This would allow a semi-conductive material manufacturer to reliably provide a customer with product quality data.

In sum, the twin detection XRD method described herein can be used as a key tool in developing unprecedented crystal alloy systems.

Although the invention has been described relative to specific embodiments thereof, there are numerous variations and modifications that will be readily apparent to those skilled in the art in light of the above teachings. For example, the present method can be expanded to include the variation of two variables to compensate for the common misalignment of the sample holder in an XRD machine. XRD measurements can be very accurate down to 1/1000 degree so that a small misalignment during the user's mounting of the sample can cause errors in the usual phiscan. The errors can be avoided by measuring XRD data during a phiscan while also varying ~ and X angles and then recording the data as a two or three-dimensional intensity plot. However, this approach is extremely time consuming and does not lend itself well to fast-paced manufacturing operations. Accordingly, this approach might be used as a periodic check on the reliability of the present method. It is therefore to be understood that, within the scope of the appended claims, the invention may be practiced other than as specifically described.

The present invention is further discussed in Y. Park, G. C. King, S. H. Choi, Rhombohedral epitaxy of cubic SiGe on trigonal c-plane sapphire, Journal of Crystal Growth 310 (2008) 2724-2731, herein incorporated by reference in its entirety.

Although the present invention has been described in detail, it should be understood that various changes, substitutions, and alterations may be readily ascertainable by those skilled in the art and may be made herein without departing from the spirit and scope of the present invention as defined by the following claims.

What is claimed as new and desired to be secured by Letters Patent of the United States is:

1. A method of generating X-ray diffraction data suitable for twin defect detection in a lattice-matched or strained epitaxial material, said epitaxial material comprising a first component having a first crystal structure, said first component being lattice matched or strained to a second component having a second crystal structure, wherein said first crystal structure has either (i) a <111> orientation relative to said second crystal structure and a {111} crystal plane normal thereto, or (ii) a {111} crystal plane at an interface of said first crystal structure with said second crystal structure and a <111> vector normal thereto, said method comprising the steps of:
   a) designating a crystal plane of said first component that is non-perpendicular to said {111} crystal plane and that produces diffraction when impinged by an X-ray beam;
   b) calculating a Bragg angle $\theta_B$ for said designated crystal plane;
   c) mounting said epitaxial material in an X-ray diffraction (XRD) system having an X-ray source for generating an X-ray beam that can impinge on said epitaxial material at a goniometer angle $\Omega$ and thereby generate X-ray diffraction, a detector having a focused direction for detecting X-ray diffraction therealong at a detector angle measured with respect to the X-ray beam, and a sample holder with a reference orientation defined thereby, wherein, when said epitaxial material is positioned in said sample holder, said [111] vector makes an angle $\chi$ relative to said reference orientation and lying in the common plane defined by said X-ray beam and said direction of focus of said detector, said angle $\chi$ being equal to $\beta$, where $\beta$ is the inter-planar angle between said {111} crystal plane said designated crystal plane;
   d) setting said goniometer angle $\Omega$ equal to $\theta_B$;
   e) setting said detector angle equal to $2*\theta_B$; and
   f) measuring the X-ray diffraction at at least one azimuthal angle $\phi$ of rotation about an axis aligned with said [111] vector, while the XRD system and said epitaxial material are in the position recited in steps c, d and e, said at least one azimuthal angle $\phi$ of rotation including at least one azimuthal angle $\phi$ of rotation at which X-ray diffraction of a twin defect occurs.

2. The method of claim 1, wherein said epitaxial material is selected from the group consisting of (1) <111> cubic crystal layer on {0001} plane of trigonal (space symmetry) crystal material layer or substrate, (2) <0001> trigonal crystal layer on {111} plane of cubic crystal material layer or substrate, (3) <111> cubic crystal layer on {0001} plane of hexagonal (space symmetry) crystal material layer or substrate, and (4) <0001> trigonal crystal layer on {111} plane of hexagonal (space symmetry) crystal material layer or substrate.

3. The method of claim 1, wherein said first component of said epitaxial material is a group IV alloy.

4. The method of claim 3, wherein said first component is silicon germanium (SiGe).

5. The method of claim 1, wherein said designated crystal plane is selected from the group consisting of {220}, {440}, {224}, {113}, {004}, {001}, {221}, {223}, {112}, {115}, {116} and {331} crystal planes.

6. The method of claim 5, wherein said designated crystal plane is the {220} crystal plane.

7. The method of claim 1, wherein said X-ray diffraction system is capable of rotating said epitaxial material about an axis aligned with said [111] vector, and wherein said measuring step further comprises continuously rotating said epitaxial material about said axis aligned with said [111] vector in order to provide an X-ray diffraction measurement at said at least one azimuthal angle $\phi$ of rotation.

8. The method of claim 7, wherein said step of rotating comprises the step of rotating said epitaxial material through an azimuthal angle $\phi$ of rotation of at least 60°.

9. The method of claim 7, wherein said step of rotating comprises the step of rotating said epitaxial material through an azimuthal angle $\phi$ of rotation of 360°.

10. The method of claim 1, further comprising providing multiple detectors or X-ray sources and arranging the angles between the detectors and X-ray sources to have the same effect as physically rotating said epitaxial material, wherein said measuring step comprises taking at least one measurement through such detectors.

11. The method of claim 1, wherein one of said components of said epitaxial material is a substrate that has a miscut or offcut angle associated therewith in the range of approximately ±10°, said method further comprising the step of adjusting said goniometer angle, said detector angle and said tilt angle based on said miscut or offcut angle.

12. The method of claim 1 further comprising checking alignment of the sample holder by recording X-ray diffraction measurements while varying $\phi$ and $\chi$ angles.

13. The method of claim 1, further comprising estimating twin defect concentration by comparing measurements at two azimuthal angles of rotation $\phi_1$ and $\phi_2$, $\phi_1$ corresponding to a twin defect and $\phi_2$ corresponding to majority crystal.

14. The method of claim 13, wherein said comparison is effected by determining the ratio of intensity of said two measurements at $\phi_1$ and $\phi_2$.

15. The method of claim 13, wherein diffraction measurements are recorded while rotating said epitaxial material through diffraction peaks at $\phi_1$ and $\phi_2$, and said comparison is effected by determining the ratio of peak area of the peak at $\phi_1$ with the peak area of the peak at $\phi_2$.

16. A method of generating X-ray diffraction data suitable for twin defect detection in a lattice-matched or strained epitaxial material, said epitaxial material comprising a first component having a first crystal structure, said first component being lattice matched or strained to a second component having a second crystal structure, wherein said first crystal structure has either (i) a <111> orientation relative to said second crystal structure and a {111} crystal plane normal thereto, or (ii) a {111} crystal plane at an interface of said first crystal structure with said second crystal structure and a <111> vector normal thereto, said method comprising the steps of:
   a) designating a crystal plane of said first component that is non-perpendicular to said {111} crystal plane and that produces diffraction when impinged by an X-ray beam;
   b) calculating a Bragg angle $\theta_B$ for said designated crystal plane;
   c) mounting said epitaxial material in an X-ray diffraction (XRD) system having an X-ray source for generating an X-ray beam that can impinge on said epitaxial material at a goniometer angle Ω and thereby generate X-ray diffraction, a detector having a focused direction for detecting X-ray diffraction therealong at a detector angle measured with respect to the X-ray beam, and a sample holder with a reference orientation defined thereby, wherein, when said epitaxial material is positioned in said sample holder, said [111] vector is aligned with said reference orientation [and lying in the common plane defined by said X-ray beam and said direction of focus of said detector];

d) setting said goniometer angle Ω equal to $\theta_B+\beta$, where $\beta$ is the inter-planar angle between said {111} crystal plane said designated crystal plane;

e) setting said detector angle equal to $\theta_B-\beta$; and f) measuring the X-ray diffraction at at least one azimuthal angle φ of rotation about an axis aligned with said [111] vector, while the XRD system and said epitaxial material are in the position recited in steps c, d and e, said at least one azimuthal angle φ of rotation including at least one azimuthal angle φ of rotation at which X-ray diffraction of a twin defect occurs.

17. The method of claim 16, wherein said epitaxial material is selected from the group consisting of (1) <111> cubic crystal layer on {0001} plane of trigonal (space symmetry) crystal material layer or substrate, (2) <0001> trigonal crystal layer on {111} plane of cubic crystal material layer or substrate, (3) <111> cubic crystal layer on {0001} plane of hexagonal (space symmetry) crystal material layer or substrate, and (4) <0001> trigonal crystal layer on {111} plane of hexagonal (space symmetry) crystal material layer or substrate.

18. The method of claim 16, wherein said first component of said epitaxial material is a group IV alloy.

19. The method of claim 18, wherein said first component is silicon germanium (SiGe).

20. The method of claim 16, wherein said designated crystal plane is selected from the group consisting of {220}, {440}, {224}, {113}, {004}, {001}, {221}, {223}, {112}, {115}, {116} and {331} crystal planes.

21. The method of claim 20, wherein said designated crystal plane is the {220} crystal plane.

22. The method of claim 16, wherein said X-ray diffraction system is capable of rotating said epitaxial material about an axis aligned with said [111] vector, and wherein said measuring step further comprises continuously rotating said epitaxial material about said axis aligned with said [111] vector in order to provide an X-ray diffraction measurement at said at least one azimuthal angle φ of rotation.

23. The method of claim 22, wherein said step of rotating comprises the step of rotating said epitaxial material through an azimuthal angle φ of rotation of at least 60°.

24. The method of claim 22, wherein said step of rotating comprises the step of rotating said epitaxial material through an azimuthal angle φ of rotation of 360°.

25. The method of claim 16, further comprising providing multiple detectors or X-ray sources and arranging the angles between the detectors and X-ray sources to have the same effect as physically rotating said epitaxial material, wherein said measuring step comprises taking at least one measurement through such detectors.

26. The method of claim 16, wherein one of said components of said epitaxial material is a substrate that has a miscut or offcut angle associated therewith in the range of approximately ±10°, said method further comprising the step of adjusting said goniometer angle, said detector angle and said tilt angle based on said miscut or offcut angle.

27. The method of claim 16 further comprising checking alignment of the sample holder by recording X-ray diffraction measurements while varying φ and χ angles.

28. The method of claim 16, further comprising estimating twin defect concentration by comparing measurements at two azimuthal angles of rotation $\phi_1$ and $\phi_2$, $\phi_1$ corresponding to a twin defect and $\phi_2$ corresponding to majority crystal.

29. The method of claim 28, wherein said comparison is effected by determining the ratio of intensity of said two measurements at $\phi_1$ and $\phi_2$.

30. The method of claim 28, wherein diffraction measurements are recorded while rotating said epitaxial material through diffraction peaks at $\phi_1$ and $\phi_2$, and said comparison is effected by determining the ratio of peak area of the peak at $\phi_1$ with the peak area of the peak at $\phi_2$.

31. A method of generating X-ray diffraction data suitable for twin defect detection in a lattice-matched or strained epitaxial material, said epitaxial material comprising a first component having a first crystal structure, said first component being lattice matched or strained to a second component having a second crystal structure, wherein said first crystal structure has either (i) a <111> orientation relative to said second crystal structure and a {111} crystal plane normal thereto, or (ii) a {111} crystal plane at an interface of said first crystal structure with said second crystal structure and a <111> vector normal thereto, said method comprising the steps of:

a) designating a crystal plane of said first component that is non-perpendicular to said {111} crystal plane and that produces diffraction when impinged by an X-ray beam;

b) calculating a Bragg angle $\theta_B$ for said designated crystal plane;

c) mounting said epitaxial material in an X-ray diffraction (XRD) system having an X-ray source for generating an X-ray beam that can impinge on said epitaxial material at a goniometer angle Ω and thereby generate X-ray diffraction, a detector having a focused direction for detecting X-ray diffraction therealong at a detector angle measured with respect to the X-ray beam, and a sample holder with a reference orientation defined thereby, wherein, when said epitaxial material is positioned in said sample holder, said [111] vector is aligned with said reference orientation [and lying in the common plane defined by said X-ray beam and said direction of focus of said detector];

d) setting said goniometer angle Ω equal to $\theta_B-\beta$, where $\beta$ is the inter-planar angle between said {111} crystal plane said designated crystal plane;

e) setting said detector angle equal to $\theta_B+\beta$; and f) measuring the X-ray diffraction at at least one azimuthal angle φ of rotation about an axis aligned with said [111] vector, while the XRD system and said epitaxial material are in the position recited in steps c, d and e, said at least one azimuthal angle φ of rotation including at least one azimuthal angle φ of rotation at which X-ray diffraction of a twin defect occurs.

32. The method of claim 31, wherein said epitaxial material is selected from the group consisting of (1) <111> cubic crystal layer on {0001} plane of trigonal (space symmetry) crystal material layer or substrate, (2) <0001> trigonal crystal layer on {111} plane of cubic crystal material layer or substrate, (3) <111> cubic crystal layer on {0001} plane of hexagonal (space symmetry) crystal material layer or substrate, and (4) <0001> trigonal crystal layer on {111} plane of hexagonal (space symmetry) crystal material layer or substrate.

33. The method of claim 31, wherein said first component of said epitaxial material is a group IV alloy.

34. The method of claim 33, wherein said first component is silicon germanium (SiGe).

35. The method of claim 31, wherein said designated crystal plane is selected from the group consisting of {220}, {440}, {224}, {113}, {004}, {001}, {221}, {223}, {112}, {115}, {116} and {331} crystal planes.

36. The method of claim 35, wherein said designated crystal plane is the {220} crystal plane.

37. The method of claim 31, wherein said X-ray diffraction system is capable of rotating said epitaxial material about an axis aligned with said [111] vector, and wherein said measuring step further comprises continuously rotating said epitaxial material about said axis aligned with said [111] vector in order to provide an X-ray diffraction measurement at said at least one azimuthal angle $\phi$ of rotation.

38. The method of claim 37, wherein said step of rotating comprises the step of rotating said epitaxial material through an azimuthal angle $\phi$ of rotation of at least 60°.

39. The method of claim 37, wherein said step of rotating comprises the step of rotating said epitaxial material through an azimuthal angle $\phi$ of rotation of 360°.

40. The method of claim 31, further comprising providing multiple detectors or X-ray sources and arranging the angles between the detectors and X-ray sources to have the same effect as physically rotating said epitaxial material, wherein said measuring step comprises taking at least one measurement through such detectors.

41. The method of claim 31, wherein one of said components of said epitaxial material is a substrate that has a miscut or offcut angle associated therewith in the range of approximately ±10°, said method further comprising the step of adjusting said goniometer angle, said detector angle and said tilt angle based on said miscut or offcut angle.

42. The method of claim 31 further comprising checking alignment of the sample holder by recording X-ray diffraction measurements while varying $\phi$ and $\chi$ angles.

43. The method of claim 31, further comprising estimating twin defect concentration by comparing measurements at two azimuthal angles of rotation $\phi_1$ and $\phi_2$, $\phi_1$ corresponding to a twin defect and $\phi_2$ corresponding to majority crystal.

44. The method of claim 43, wherein said comparison is effected by determining the ratio of intensity of said two measurements at $\phi_1$ and $\phi_2$.

45. The method of claim 43, wherein diffraction measurements are recorded while rotating said epitaxial material through diffraction peaks at $\phi_1$ and $\phi_2$, and said comparison is effected by determining the ratio of peak area of the peak at $\phi_1$ with the peak area of the peak at $\phi_2$.

* * * * *